United States Patent [19]

Fogel et al.

[11] Patent Number: 4,537,762
[45] Date of Patent: Aug. 27, 1985

[54] HAIR COMPOSITIONS CONTAINING MIXTURES OF QUATERNARY AMMONIUM COMPOUNDS AND TERTIARY AMINE SALTS OF LONG-CHAIN ACIDS

[75] Inventors: Arnold W. Fogel, Park Ridge; Albert Zofchak, Matawan, both of

[73] Assignees: Bernel Chemical Co., Waldwick; Alzo, Inc., Matawan, both of N.J.

[21] Appl. No.: 551,484

[22] Filed: Nov. 14, 1983

[51] Int. Cl.³ .............................................. A61K 7/06
[52] U.S. Cl. ...................................... 424/70; 514/784
[58] Field of Search ........................................... 424/70

[56] References Cited

U.S. PATENT DOCUMENTS

| | | | |
|---|---|---|---|
| 2,089,212 | 8/1937 | Kritchensky | 424/326 |
| 2,228,986 | 1/1941 | De Groate et al. | 252/316 |
| 2,484,146 | 10/1948 | Barker | 252/316 X |
| 2,514,954 | 7/1950 | Johnson et al. | 252/106 |
| 2,663,648 | 12/1953 | Jelling | 106/273 |
| 2,681,354 | 6/1954 | Kelley et al. | 260/404.5 |
| 3,424,771 | 1/1969 | Libby et al. | 260/404.5 |
| 3,562,170 | 2/1971 | Zorayan et al. | 424/70 |
| 3,563,901 | 2/1971 | Cratty | 424/70 |
| 3,590,122 | 6/1971 | Roberts et al. | 424/70 |
| 3,822,312 | 7/1974 | Sato et al. | 424/70 |

FOREIGN PATENT DOCUMENTS

| | | | |
|---|---|---|---|
| 46-5838 | 2/1971 | Japan | 424/70 |
| 48-18810 | 6/1973 | Japan | 424/70 |
| 823303 | 11/1959 | United Kingdom | 424/70 |

*Primary Examiner*—Dale R. Ore
*Attorney, Agent, or Firm*—Anthony D. Cipollone

[57] ABSTRACT

This invention is concerned with various physical mixtures of quaternary ammonium compounds and tertiary amine salts of long-chain acids.

These self-emulsifiable and self-dispersing mixtures exhibit synergistically enhanced properties including: surfactant and emollient properties, anti-static properties, anti-tangle properties, lubricant properties, and film forming properties.

These unique properties and characteristics are utilized in various hair and skin conditioner formulations.

4 Claims, No Drawings

HAIR COMPOSITIONS CONTAINING MIXTURES OF QUATERNARY AMMONIUM COMPOUNDS AND TERTIARY AMINE SALTS OF LONG-CHAIN ACIDS

BACKGROUND OF THE INVENTION

1. FIELD OF THE INVENTION

This invention relates to the unique effects and characteristics of a physical mixture of quaternary ammonium compounds and tertiary amine salts of long-chain acids in varying concentrations in hair and skin conditioner formulations. The concentrations are based on weight-to-weight ratios of 60/40 to 90/10 respectively. These varied physical mixtures are particularly useful in hair and skin conditioner formulations. They have self-emulsifying and self-dispersing properties, surfactant properties, lubricating, anti-static properties, and film forming properties, anti-tangle properties.

The preferred embodiment of the invention is a 60/40 weight-to-weight ratio of the quaternary ammonium compound/tertiary amine salts of long-chain acids where the quaternary ammonium compound has the following structure:

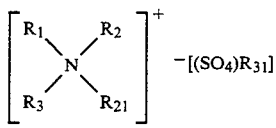

Where:

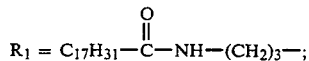

$R_2 = R_{21} = CH_3-$; $R_3 = R_{31} = C_2H_5-$ and the tertiary amine salts of long-chain acids has the following structure:

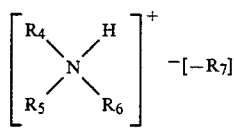

Where: $R_4 = C_{12}H_{25}-$; $R_5 = R_6 = CH_3-$;

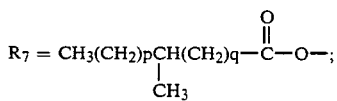

Where $p + q = 14$.

2. DESCRIPTION OF THE PRIOR ART

Quaternary ammonium compounds and tertiary amine salts of long-chain acid compounds are well known products in the chemical literature.

The use of quaternary ammonium compounds has been extensive in hair rinse formulations. A recent literature search does not disclose the use of tertiary amine salts of long-chain acid compounds in any hair rinse formulations.

The use of quaternary ammonium compounds in conjunction with tertiary amine salts of long-chain acid compounds was not found in any search involving such a combination for use in skin and hair conditioner formulations.

U.S. Pat. No. 30,874 to Dasher et al. describes the use of quaternary ammonium compounds in the pretreatment of hair before useing an anionic shampoo.

Hair cream rinse formulations containing quaternary ammonium salts have been described in U.S. Pat. No. 3,959,461 by Bailey et al.

U.S. Pat. No. 4,096,243 by Feinland et al. describes a composition for lightening hair using a quaternary amine.

Liquid hair rinse containing a quaternary ammonium salt and a synthetic secondary alcohol is described in U.S. Pat. No. 4,165,369 by Watanabe et al.

U.S. Pat. No. 4,187,289 by Eckhardt deals with the use of diester/amine adducts and quaternary ammonium salts as after-rinse softeners and after-shampoo hair conditioners.

A hair conditioning article and its use is described in U.S. Pat. No. 4,206,195 by Bolich et al.

The use of quaternary ammonium compounds in hair conditioner formulations is known in the art. Their blend with tertiary amine salts of long-chaim acid compounds and their blend in varying ratios introduces uniqueness in properties and uses in this invention.

OBJECTS & SUMMARY OF THE INVENTION

It is the object of this invention to provide novel physical compositions of quaternary ammonium compounds and tertiary amine salts of long-chain acid compounds having a unique property making these compositions uniquely suitable in various hair and skin conditioner formulations.

It is the further objects of this invention to provide mixtures of quaternary ammonium commpounds and tertiary amine salts of long-chain acid compounds in varying weight-to-weight ratios of 60/40 to 90/10 respectively.

It is believed that the uniqueness of this invention is the use of the combination of quaternary ammonium compounds and tertiary amine salts of long-chain acid compounds which synergistically enhance each component's unique properties.

It is believed that the mixture of the two compounds together uniquely enhance the properties of each other. By mixing a water soluble quaternary ammonium compound with an oil soluble tertiary amine salt of long-chain acids a unique system unknown previously in skin and hair conditioner formulations is formed. The oil soluble salt moiety plasticizes the crisp film left by the water soluble moiety as it adds its own anti-tangle emollient property in synergistic fashion.

It is further believed that these self-emulsifiable and self-dispersing compositions in these inventions have the surfactant, emollient, anti-static, anti-tangle, lubricant, and film forming properties which make the compositions particularly suited for hair and skin conditioner formulations.

The preferred embodiment of this invention is as follows: 60%/40% weight-to-weight ratio of a quaternary ammonium compound/tertiary amine salts of long-chain acid compounds where the quaternary ammonium compound has the following structure:

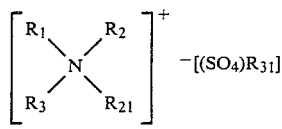  III

Where:

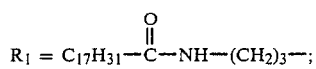

$R_2=R_{21}=CH_3—$; $R_3=R_{31}=C_2H_5—$ and the tertiary amine salts of long-chain acids has the following structure:

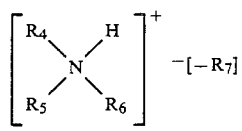  IV

Where: $R_4=C_{12}H_{25}—$; $R_5=R_6=CH_3—$;

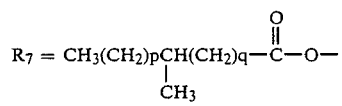

Where $p+q=14$.

DETAILED DESCRIPTION OF THE INVENTION

Quaternary ammonium compounds are well known in the literature. Their formation is usually by a reaction of an alkylhalide with ammonia with subsequent reaction of the amine produced with another alkylhalide to produce the amine of the next higher class as follows:

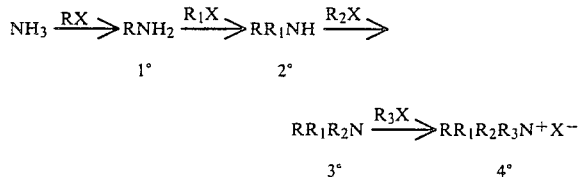

In the instant invention, the preferred embodiment of the invention, the quaternary ammonium compound is a sulfate produced as follows:

Sunflower Seed Oil or Safflower Oil whose major reactive constituent is linoleic acid (V) is reacted with dimethyl amino propylamine (VI) in the presence of a catalyst (either Sodium Methylate or Sodium Borohydride) to produce the corresponding amide at temperatures between 125°–165° C. at pressures of 1 to 2 atmospheres to produce the corresponding amide (VII).

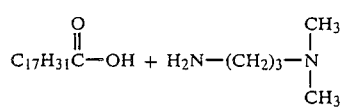

[Sunflower Seed Oil]  V

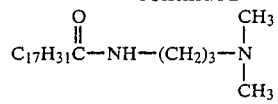  VII

This amide (VII) is then reacted with diethyl sulfate at ambient pressure under nitrogen at a temperature of 60°–75° C. to produce the quaternary ammonium sulfate.

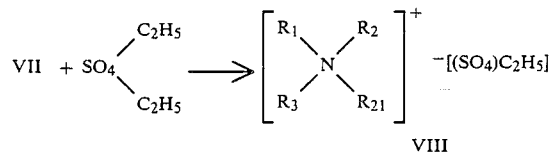  VIII

Where:

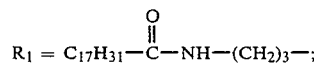

$R_2=R_{21}=CH_3—$; $R_3=C_2H_5—$.

Tertiary amine salts of long-chain acids are known. They have the formula

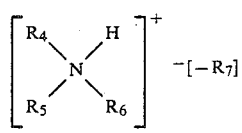  IX wherein $R_4$ is selected from the group consisting of saturated and unsaturated aliphatic groups containing from about 8 to about 22 carbon atoms,

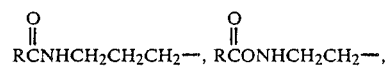

$RN(CH_3)CH_2CH_2CH_2—$, $RN(CH_2CH_2OH)CH_2CH_2—$,

$CH_3O[CH_2CH(CH_3)O]_{1-5}CH_2CH_2CH_2—$, $H[O(CH_3)CHCH_2]_{3-8}$, $H[O(CH_3)CHCH_2]_{3-8}OHC_2CH_2—$, $RCHOHCH_2$, and $ROCH_2CH_2CH_2$, wherein R represents a saturated or unsaturated aliphatic group containing from about 8 to 22 carbon atoms; $R_6$ is selected from the group consisting of saturated and unsaturated groups containing from one to about two carbon atoms and $H(OCH_2CH_2)_{1-15}$, $R_5$ is selected from the group consisting of saturated and unsaturated aliphatic groups containing from about 1 about 22 carbon atoms,

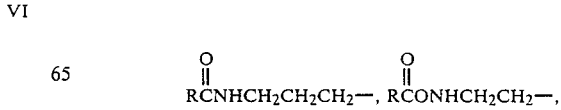

$RN(CH_3)_2CH_2CH_2CH_2—$,
$RN(CH_2CH_2OH)CH_2CH_2CH_2—$, $$\overset{O}{\underset{\|}{R C O}} C H_2 C H_2 -,$$

$CH_3O[CH_2CH(CH_3)O]_{1-5}CH_2CH_2CH_2-$, $H[O(CH_3)CHCH_2]_{3-8}$, $H[O(CH_3)CHCH_2]_{3-8}OCH_2CH_2-$, $RCHOHCH_2$, $ROCH_2CH_2CH_2$, saturated and unsaturated groups containing from one to about two carbon atoms and $H(OCH_2CH_2)_{1-15}$, and $R_7$ is selected from the group consisting of $$R-\overset{O}{\underset{\|}{C}}-O,$$

$RCH=CH_2SO_3-$, $RCONHCH(CH_3)CO_2-$, $ROSO_3-$, $RC_6H_5SO_3-$, $RNHCOCH=CHCO_2-$, isostearic acid residue, ricinoleic acid residue, and dimer acid residue, wherein R represents a saturated or unsaturated aliphatic group containing from about 8 to about 18 carbon atoms.

The preferred embodiment of the invention uses dimethyl lauramine isostearate but any of the above tertiary amine salts of long-chain acids may be used.

Dimethyl lauramine isostearate is produced by reacting dimethyl lauramine (X) with isostearic acid (XI) under high temperature and vacuum to produce a tertiary amine salt.

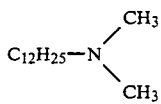   X

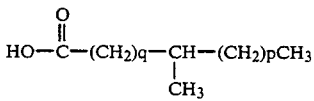   XI

Isostearic Acid
Where p + q = 14.

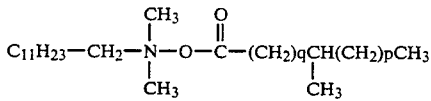   XII

VIII and XII are physically blended by mixing together and stirring in warm environment to give various weight-to-weight ratios of VIII/XII 60/40 to 90/10, the preferred embodiment being 60/40 of VIII/XII.

This blending gives formulations using these compositions their unique properties including: self-emulsification, emollient properties, surfactant properties, antitangle properties, anti-static properties, film forming properties, and lubricating properties.

These unique properties make these compositions in this invention applicable to hair and skin conditioner formulations.

EXAMPLES

The following formulations are intended to be merely illustrative of the invention and its versatility and not in limitation thereof.

Unless otherwise indicated, all quantities are on a weight basis.

Parapel HC is the trade name used for the preferred embodiment of the instant invention 60/40 ratio of VIII/XII.

EXAMPLE 1

| CREME RINSE FORMULATION* | |
|---|---|
| | Percentage by Weight |
| PHASE A (Heat to 85° C.) | |
| Cetyl Alcohol | 1.5 |
| Stearyl Alcohol | 1.5 |
| Parapel HC (Bernel Chemical) | 2.5 |
| Arosurf TA-100 | 1.0 |
| PHASE B (Heat to 85° C. and disperse well) | |
| Water, deionized | 92.9 |
| Cellosize QP30,000Hi | 0.5 |
| PHASE C | |
| Kathon CG (Rohm & Haas) | 0.1 |
| | 100.0 |

PROCEDURE:
Add Phase A to Phase B. Mix well at 85° C., then begin cooling. Continue mixing (avoid aeration) and at 50° C., add Phase C, mix until cool.
*NOTE:
Put on, rinse off type. Use between ½ and 1 oz.

EXAMPLE 2

| HAIR CONDITIONER | |
|---|---|
| | Percentage by Weight |
| PHASE A (Heat to 85° C. and mix well) | |
| (1) Glyceryl Stearate, pure | 4.00 |
| (1) Foamine 1880 (DMAPS) | 0.60 |
| Bernel Ester DOM | 2.00 |
| (2) Hetester ISS | 2.00 |
| (5) Cetyl Alcohol | 1.00 |
| Parapel HC | 2.50 |
| PHASE B (Heat to 85° C. and disperse) | |
| Water, deionized | 85.05 |
| (3) Cellosize QP 30000 (Hi) | 0.50 |
| Parapel LAM-100 | 2.00 |
| PHASE C | |
| Lactic Acid, USP | 0.25$^{(n)}$ |
| PHASE D | |
| (4) Kathon CG | 0.10 |
| | 100.00% Total |

PROCEDURE:
Add Phase C to Phase B and mix well. Continue to mix and slowly add Phase A. Mix well without aeration at 80° C., then cool to 50° C. and add Phase D. Cool and mix to 30° C.
(n) The desired pH is 4.8–5.2 and can be adjusted in Phase C.
SUPPLIERS:
(1) ALZO Inc.
(2) Heterene Chemical Co. Inc.
(3) Union Carbide Corp.
(4) Rohm & Haas Inc.
(5) Henkel Corporation

What is claimed is:
1. A hair treating composition seleereo from the group consisting of creme rinses and conditioners comprising component (a) a quaternary ammonium compound of the formula

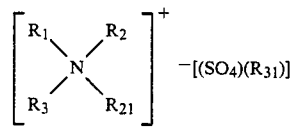

in which

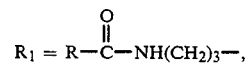

where R is an alkyl or alkenyl chain of 8 to 22 carbon atoms, $R_2$ and $R_{21}$ are methyl or ethyl, and $R_3$ and $R_{31}$ are alkyl chains of 1 to 3 carbons, and component (b) a tertiary amine salt of a long-chain acid of the formula

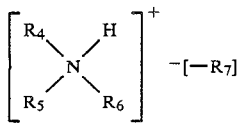

wherein $R_4$ is selected from the group consisting of saturated and unsaturated aliphatic groups containing from about 8 to about 22 carbon atoms,

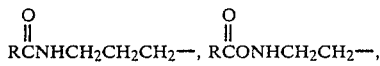

$RN(CH_3)CH_2CH_2CH_2-$,
$RN(CH_2CH_2OH)CH_2CH_2CH_2-$,

$CH_3O[CH_2CH(CH_3)O]_{1-5}CH_2CH_2CH_2-$, $H[O(CH_3)CHCH_2]_{3-8}$, $H[O(CH_3)CHCH_2]_{3-8}OCH_2CH_2-$, $RCHOHCH_2$, and $ROCH_2CH_2CH_2$, wherein R represents a saturated or unsaturated aliphatic group containing from about 8 to about 22 carbon atoms; $R_6$ is selected from the group consisting of saturated and unsaturated groups containing from one to about two carbon atoms and $H(OCH_2CH_2)_{1-15}$, $R_5$ is selected from the group consisting of saturated and unsaturated aliphatic groups containing from about 1 to about 22 carbon atoms,

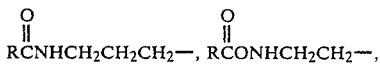

$RN(CH_3)_2CH_2Ch_2CH_2-$,
$RN(CH_2CH_2OH)CH_2CH_2CH_2-$,

$CH_3O[CH_2CH(CH_3)O]_{1-5}CH_2CH_2CH_2-$, $H[O(CH_3)CHCH_2]_{3-8}$, $H[O(CH_3)CHCH_2]_{3-8}OCH_2CH_2-$, $RCHOHCH_2$, $ROCH_2CH_2CH_2$, saturated and unsaturated groups containing from one to about two carbon atoms and $H(OCH_2CH_2)_{1-15}$, and $R_7$ is selected from the group consisting of

$RCH=CH_2SO_3-$, $RCONHCH(CH_3)CO_2-$, $ROSO_3$, $RC_6H_5SO_3-$, $RNHCOCH=CHCO_2$, isostearic acid residue, ricinoleic and residue, and dimer acid residue, wherein R represents a saturated or unsaturated aliphatic group containing from about 8 to about 18 carbon atoms, the weight-to-weight ratio of the quaternary ammonium compound/tertiary amine salt of long-chain acid varying from 60/40 to 90/10.

2. The mixture of claim 1 in which component (a) the quaternary ammonium compound has the formula

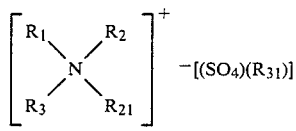

where:

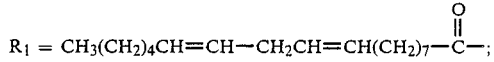

$R_2$ and $R_{21}=CH_3-R_3$ and $R_{31}=C_2H_5-$.

3. The mixture of claim 1 which the component (b) the tertiary amine salt of a long-chain acid has the formula

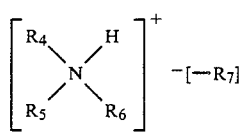

where: $R_4=C_{12}H_{25}-$; $R_5$ and $R_6=CH_3-$;

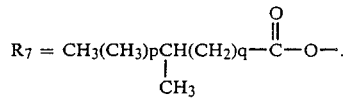

4. The mixture according to claim 1 in which the component (a) the quaternary ammonium compound has the formula

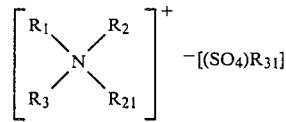

in which

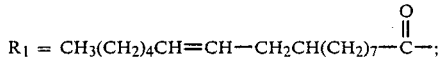

$R_2$ and $R_{21}=CH_3-$; $R_3$ and $R_{31}=C_2H_5-$; and, component (b) the tertiary amine salt of a long-chain acid has the formula

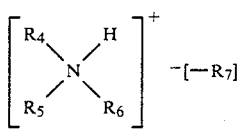

in which $R_4=C_{12}H_{25}-$; $R_5$ and $R_6=CH_3-$;

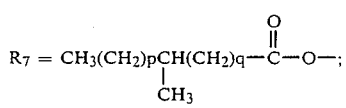

where $p+q=14$, and the weight/weight ratio of component (a)/Component (b) is 60/40.

* * * * *